US011133026B2

(12) United States Patent
Gordon et al.

(10) Patent No.: US 11,133,026 B2
(45) Date of Patent: Sep. 28, 2021

(54) NATURAL LANGUAGE PROCESSOR FOR USING SPEECH TO COGNITIVELY DETECT AND ANALYZE DEVIATIONS FROM A BASELINE

(71) Applicant: INTERNATIONAL BUSINESS MACHINES CORPORATION, Armonk, NY (US)

(72) Inventors: Michael S. Gordon, Yorktown Heights, NY (US); James Humble, Hartsdale, NY (US); Tim Rumbell, Raleigh, NC (US); Ryan T. Gordon, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 133 days.

(21) Appl. No.: 16/239,988

(22) Filed: Jan. 4, 2019

(65) Prior Publication Data
US 2020/0219529 A1    Jul. 9, 2020

(51) Int. Cl.
*G10L 25/66* (2013.01)
*G10L 15/30* (2013.01)
(Continued)

(52) U.S. Cl.
CPC ............ *G10L 25/66* (2013.01); *A61B 5/4064* (2013.01); *A61B 5/4803* (2013.01);
(Continued)

(58) Field of Classification Search
CPC ... G10L 25/66; G10L 15/1815; G10L 15/183; G10L 15/22; G10L 15/30; G06N 20/00;
(Continued)

(56) References Cited

U.S. PATENT DOCUMENTS 8,346,688 B2   1/2013  Carroll et al.
8,897,437 B1*  11/2014  Tan .................. H04M 3/5175
                                                      379/265.07
(Continued)

FOREIGN PATENT DOCUMENTS

CN    105118519 A   12/2015
CN    108877841 A   11/2018
(Continued)

OTHER PUBLICATIONS

International Search Report and Written Opinion for Application No. PCT/IB2019/060605 dated Mar. 25, 2020, 9 pages.
(Continued)

*Primary Examiner* — Mohammad K Islam
(74) *Attorney, Agent, or Firm* — Cantor Colburn LLP; Joseph Petrokaitis

(57) ABSTRACT

A natural language processing system for analyzing speech includes a computer processing device configured to receive recorded speech of a person. The computer processing device constructs a baseline speech model of the person, the baseline speech model of the person including a property of speech based on a personal attribute of the person, compares current recorded speech of the person to the baseline speech model of the person to determine a deviation of the property of speech therebetween, and determines if the deviation of the property of speech meets a threshold of the property of speech that is defined for a disorder.

16 Claims, 3 Drawing Sheets

(51) Int. Cl.
*G10L 15/22* (2006.01)
*G10L 15/18* (2013.01)
*G06N 20/00* (2019.01)
*A61B 5/00* (2006.01)
*G10L 15/183* (2013.01)

(52) U.S. Cl.
CPC .......... *A61B 5/7267* (2013.01); *G06N 20/00* (2019.01); *G10L 15/183* (2013.01); *G10L 15/1815* (2013.01); *G10L 15/22* (2013.01); *G10L 15/30* (2013.01)

(58) Field of Classification Search
CPC .... A61B 5/4064; A61B 5/4803; A61B 5/7267
See application file for complete search history.

(56) References Cited

U.S. PATENT DOCUMENTS

| | | | | |
|---|---|---|---|---|
| 9,311,932 | B2* | 4/2016 | Carter | G10L 25/78 |
| 9,754,586 | B2* | 9/2017 | Deligne | G10L 15/19 |
| 9,953,650 | B1* | 4/2018 | Falevsky | G06F 3/011 |
| 10,269,374 | B2* | 4/2019 | Spizzo | A61B 5/743 |
| 10,475,451 | B1* | 11/2019 | Lynch | G10L 15/22 |
| 10,573,312 | B1* | 2/2020 | Thomson | G10L 15/26 |
| 10,726,830 | B1* | 7/2020 | Mandal | G10L 15/16 |
| 10,777,189 | B1* | 9/2020 | Fu | G10L 15/30 |
| 10,896,428 | B1* | 1/2021 | Balasubramaniam | G06Q 30/016 |
| 2007/0276270 | A1 | 11/2007 | Tran | |
| 2008/0146892 | A1 | 6/2008 | LeBoeuf | |
| 2008/0249779 | A1* | 10/2008 | Hennecke | G10L 15/22 704/270 |
| 2010/0286490 | A1* | 11/2010 | Koverzin | G08B 31/00 600/301 |
| 2011/0245707 | A1 | 10/2011 | Castle et al. | |
| 2015/0017161 | A1* | 1/2015 | Schneider | C07K 14/70575 424/134.1 |
| 2015/0112232 | A1 | 4/2015 | Quatieri | |
| 2015/0302850 | A1* | 10/2015 | Lebrun | G06F 40/35 704/243 |
| 2015/0351680 | A1* | 12/2015 | Gordon | A61B 5/7275 600/595 |
| 2016/0071517 | A1* | 3/2016 | Beaver | G10L 15/22 704/9 |
| 2016/0125748 | A1* | 5/2016 | Ashford | G16H 15/00 434/236 |
| 2017/0037475 | A1* | 2/2017 | Ho | C12Q 1/6883 |
| 2017/0053665 | A1* | 2/2017 | Quatieri, Jr. | G10L 25/66 |
| 2017/0116185 | A1* | 4/2017 | Erickson | G06F 40/51 |
| 2017/0188979 | A1* | 7/2017 | Volpe | A61B 5/6804 |
| 2017/0206805 | A1* | 7/2017 | Salamini | A61B 5/7455 |
| 2017/0258390 | A1 | 9/2017 | Howard | |
| 2018/0075845 | A1* | 3/2018 | Kochura | G10L 25/48 |
| 2018/0125415 | A1* | 5/2018 | Reed | H04R 25/30 |
| 2018/0196919 | A1* | 7/2018 | Abou Mahmoud | G16H 10/60 |
| 2018/0205726 | A1* | 7/2018 | Chari | G10L 17/02 |
| 2018/0296092 | A1* | 10/2018 | Hassan | G10L 25/66 |
| 2018/0322961 | A1* | 11/2018 | Kim | A61B 5/1123 |
| 2018/0338710 | A1* | 11/2018 | Tas | G06K 9/00268 |
| 2018/0349560 | A1* | 12/2018 | McCloskey | G10L 25/66 |
| 2018/0350395 | A1* | 12/2018 | Simko | G10L 15/065 |
| 2018/0358009 | A1* | 12/2018 | Daley | G06F 3/167 |
| 2019/0305976 | A1* | 10/2019 | Bender | G10L 25/63 |
| 2019/0327330 | A1* | 10/2019 | Natarajan | G06F 9/453 |
| 2019/0348065 | A1* | 11/2019 | Talwar | G10L 15/22 |
| 2020/0051560 | A1* | 2/2020 | Yi | G10L 15/063 |
| 2020/0098376 | A1* | 3/2020 | Tas | G10L 25/66 |
| 2020/0229752 | A1* | 7/2020 | Sumi | G10L 25/66 |

FOREIGN PATENT DOCUMENTS

| | | |
|---|---|---|
| EP | 2215965 A1 | 8/2010 |
| WO | 201768582 A1 | 4/2017 |

OTHER PUBLICATIONS

Ahmed, S., et al., "Connected speech as a marker of disease progression in autospy-proven Alzheimer's disease," 2013, Brain: A Journal of Neurology, vol. 136, pp. 3727-3737.
Busacco, D., "Normal Communication Changes in Older Adults," Jan./Feb. 1999, Let's Talk for People With Special Communication Needs, No. 72, 2 pages.
http://www.strokecenter.org/patients/about-stroke/stroke-statistics/.
https://www.alz.org/documents/national/submitted-testimony-050113.pdf.
https://www.alz.org/facts.
Skodda, S., et al., "Progression of Voice and Speech Impairment in the Course of Parkinson's Disease: A Longitudinal Study," Research Article, Hindawi Publishing Corportaion Parkinson's Disease, vol. 2013, Article ID. 389195, 8 pages.
Horner, R.D., "The high cost of stroke to society, the family, and the patient," 1998, Pharmacotherapy, vol. 18 (3 Pt 2), 87S-86S, Abstract Only.

* cited by examiner

NATURAL LANGUAGE PROCESSOR FOR USING SPEECH TO COGNITIVELY DETECT AND ANALYZE DEVIATIONS FROM A BASELINE

BACKGROUND

The present invention generally relates to computing systems that perform natural language processing, and more specifically, to computing systems that use natural language processing (NLP) to evaluate a person's speech over time, cognitively detect subtle variations of the person's speech, and utilize the cognitively detected speech variations to aid in determining whether the person has a cognitive disorder.

NLP generally identifies a suite of computer-based tools that draw on the fields of computer science, artificial intelligence, and computational linguistics to manage the interactions between computers and humans using language (i.e., natural language). As such, NLP systems are related to the area of human-computer interaction. Among the challenges in implementing NLP systems is enabling computers to derive meaning from NL inputs (e.g., speech), as well as the effective and efficient generation of NL outputs.

SUMMARY

Embodiments of the present invention are directed to a natural language processing system for analyzing speech. A non-limiting example of the system includes a computer processing device configured to receive recorded speech of a person. The computer processing device constructs a baseline speech model of the person, the baseline speech model of the person including a property of speech based on a personal attribute of the person, compares current recorded speech of the person to the baseline speech model of the person to determine a deviation of the property of speech therebetween, and determines if the deviation of the property of speech meets a threshold of the property of speech that is defined for a disorder.

Embodiments of the present invention are directed to a computer-implemented method that processes natural language for analyzing speech. A non-limiting example of the computer-implemented method includes receiving recorded speech of a person, constructing a baseline speech model of the person, the baseline speech model of the person including a property of speech based on a personal attribute of the person, comparing current recorded speech of the person to the baseline speech model of the person to determine a deviation of the property of speech therebetween, and determining if the deviation of the property of speech meets a threshold of the property of speech that is defined for a disorder.

Embodiments of the invention are directed to a computer program product which processes natural language for analyzing speech. A non-limiting example of the computer program product includes a computer readable storage medium having program instructions embodied therewith, where the program instructions are executable by a computer to cause the computer to perform a method. The method includes receiving recorded speech of a person, constructing a baseline speech model of the person, the baseline speech model of the person including a property of speech based on a personal attribute of the person, comparing current recorded speech of the person to the baseline speech model of the person to determine a deviation of the property of speech therebetween, and determining if the deviation of the property of speech meets a threshold of the property of speech that is defined for a disorder.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
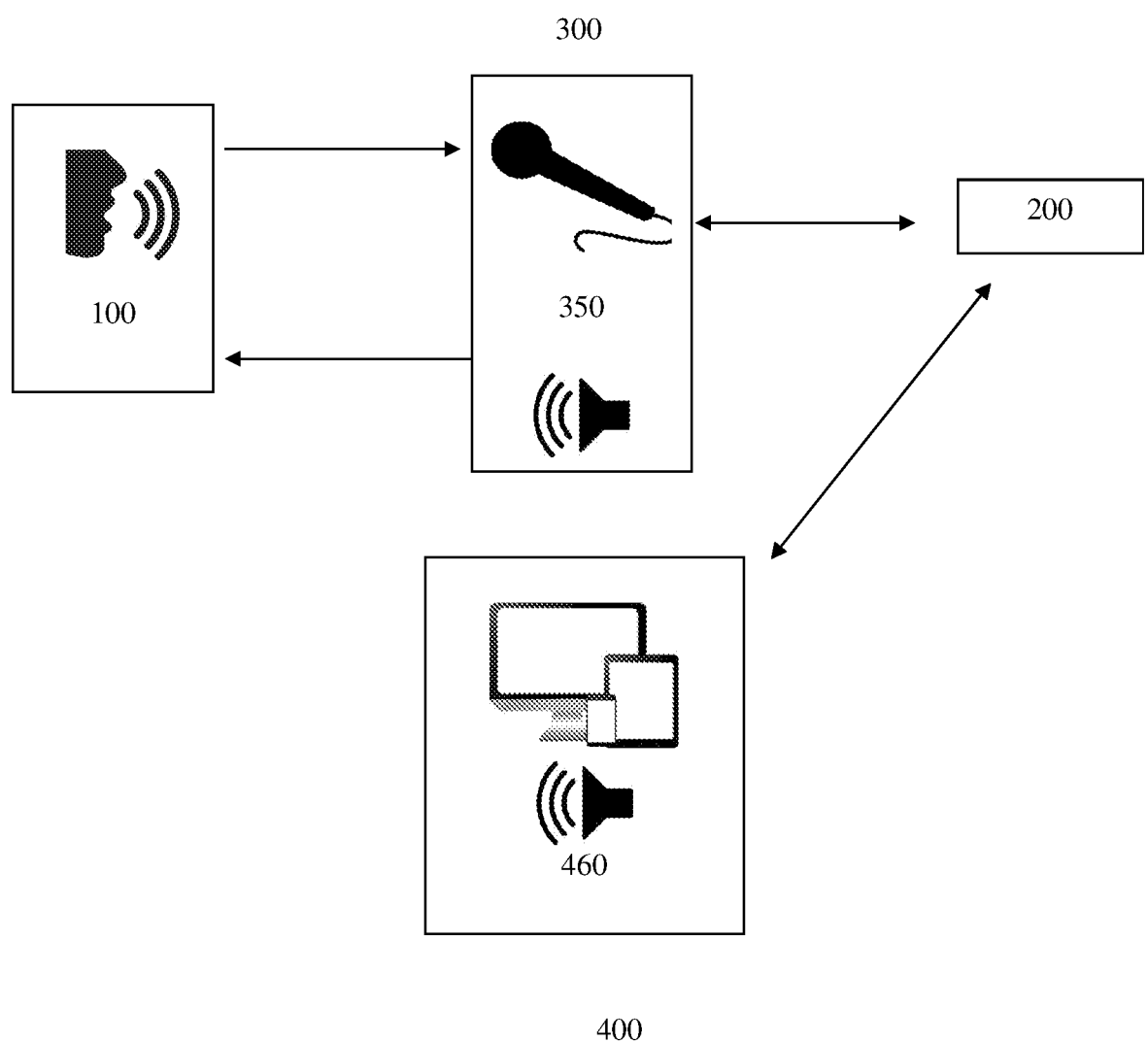
FIG. 1 depicts a system of speech detection and analysis according to an embodiment of the invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, NLP question & answer (NLP Q&A) systems answer NL questions by querying data repositories and applying elements of language processing, information retrieval and machine learning to arrive at a conclusion. NLP Q&A systems assist humans with certain types of semantic query and search operations, such as the type of natural question-and-answer paradigm of a medical environment. An example NLP Q&A system is IBM's DeepQA technologies, which are able to understand complex questions input to the system in natural language, and are able to answer the questions to augment human handling of the same questions within a given environment, such as a medical inquiry and diagnostic paradigm.

An anatomical or physiological characteristic of a person can be measured in the person's speech. Voice is generally considered sound uttered by the mouth, especially that uttered by human beings in speech where the sound possesses some property or characteristic. Speech is generally considered the faculty of uttering articulate sounds or words such as the ability to speak or to use vocalizations to communicate. Hereinafter, "voice" and "speech" may be used interchangeably unless otherwise contradicted within the context of the reference thereto.

Quantitative and qualitative properties and characteristic of a person's voice or speech can include, but are not limited to cadence, tone, pitch, speed, word content, word complexity, pauses, periodicity, volume, semantic structure, sound produced during speech, coherency, etc. The existence of or a progression in a property or characteristic of a person's voice or speech over time can be expected due to factors such as aging, tooth loss or compromised dentition, speech impediments such as stuttering, etc.

The existence, absence, change or progression of a property or characteristic in a person's speech outside of what is expected, can be an early signature of a brain related illness or injury or a neurological disorder. For example, aphasia and verbal apraxia are symptoms of stroke. As other examples, progression of voice and speech impairment is a symptom of Parkinson's disease, and progression of syntactic complexity impairment, forgetting of familiar words or the location of everyday objects, general problems with memory and concentration, and trouble remembering new names are symptoms of Alzheimer's disease.

The timely recognition and diagnosis of brain related illnesses and injuries and neurological disorders and is critical for treatment to be administered effectively. For example, the early detection and treatment of ischemic stroke can limit brain damage and greatly improve a patient's outcome. As another example, because diagnoses of Alzheimer's disease are more accurate early in the disease's progression, early detection can allow for treatment to be more effective and in some cases can reverse some cognitive decline.

Early detection of a change or progression in someone's speech generally requires some knowledge of the person's previous "normal" speech. A friend or family member who is in regular contact with a family member may be able to notice a subtle change or progression in a family member's speech. For example, as symptoms of Alzheimer's disease, a friend or family member may notice extended pauses in a person's speech (agnosia), or the forgetting of names etc. due to memory loss. As another example, as symptoms of Parkinson's disease, a friend or family member may notice hoarseness, softer tones, imprecise articulation and differences in the rate of spoken words, and pauses between spoken words.

However, if a person lives alone or rarely interacts with friends and family, a subtle change or progression in the person's speech can go unnoticed for a relatively long period of time such that the early warning of an illness or disorder can be limited. Similarly, where a medical professional such as a doctor is not in regular contact with the family member, a subtle change in the family member's speech may not be noticed by the doctor because they are unfamiliar with the person's previous "normal" speech such that the early warning of an illness or disorder can be limited.

Even if a friend or family member or a medical professional who is in regular contact with a family member may be able to notice a subtle change or progression in a family member's speech, the individual may not represent their observations objectively or independently. For example, an individual may not accurately report or fully reveal an observed change or progression in a person's speech to protect the person for legal or employment purposes, or to protect the individual's own personal interests.

Limited access to a recording of a person's "normal" or "baseline" speech can frustrate detection of a change or progression in the person's speech. For example, a medical professional who is not in regular contact with a patient or who encounters the patient for the first time may not know how the patient's "normal" or previous speech actually sounds, and may not have access to or be able to listen to an audio version of the recording of the patient's "normal" or previous speech. Where there is no recording of the patient's speech to define "normal" or previous speech for that patient, the medical professional may not know how the speech of a person similarly situated in age, demographics, dialects, medical condition, etc. to the patient should generally sound. In this case, an audio version of the recording of speech of such similarly-situated person may be helpful to the medical professional.

Limited access to a person's speech recordings which have been collected over time can further limit analysis and detection of an illness, injury or disorder and administration of a speech therapy therefor. For example, where different speech recordings are saved or stored in various places, analysis of the speech recordings can be frustrated such that a stutter can go undetected and there is a missed opportunity for providing exercises or treatment to the person for the stutter. Even where the stutter is detected, the analysis may not prompt the person in real-time to perform the exercises, especially in a non-clinical environment such as in the person's home or regular living areas.

Turning now to an overview of the aspects of the invention, one or more embodiments of the invention address the above-described shortcomings of the prior art by providing a NLP system and related methodologies configured to cognitively analyze speech recordings to generate objective classifications of an individual person's speech to be used as a baseline "normal" speech of the individual person, from which a change or progression of a property or characteristic in the person's speech outside of what is expected can be determined. Furthermore, the NLP systems and methods in accordance with aspects of the invention use the cognitive analysis to diagnose an illness, injury or disorder and to prompt an individual to initiate exercises or treatment related to such diagnosis.

The above-described aspects of the invention address the shortcomings of the prior art by using machine learning algorithms to classify a person's baseline "normal" speech based on cognitive analysis of training data that can include a recording of that person's speech and/or a recording of speech for one or more individuals similarly situated in age, demographics, dialects, medical condition, etc. to the person, including what can be expected in one's speech owing to factors such as aging, tooth loss or compromised dentition, and speech impediments. Such classification of the person's baseline "normal" speech avoids subjective observation of the person's speech and customizes a "baseline" from which a change or progression in the person's speech outside of what is expected can be determined.

In accordance with aspects of the invention, the NLP system can include a classifier (or classifier algorithm) configured and arranged to use machine learning algorithms to apply machine learning techniques to the above-described training data. In aspects of the invention, the classifier (or classifier algorithm) uses the machine learning algorithms to extract features from the training data in order to "classify" the training data and uncover relationships between and among the classified training data. The classifier uses the classified training data and the uncovered relationships between and among the classified training data to create a model of the person's baseline normal speech, which can be subsequently compared to the person's actual speech to detect deviations from the baseline norm. Examples of suitable implementations of the classifier and machine learning algorithms of the NLP system include but are not limited to neural networks, support vector machines (SVMs), logistic regression, decision trees, hidden Markov Models (HMMs), etc. The learning or training performed by the classifier can be supervised, unsupervised, or a hybrid that includes aspects of supervised and unsupervised learning. Supervised learning is when training data are already available and classified/labeled. Unsupervised learning is when training data are not classified/labeled so they must be developed through iterations of the classifier. Unsupervised learning can utilize additional learning/training methods including, for example, clustering, anomaly detection, neural networks, deep learning, and the like.

In aspects of the invention, the classifier of the NLP system can be configured to apply confidence levels (CLs) aspects of the baseline normal speech model. When the classifier determines that a CL in an aspect of the baseline normal speech model is below a predetermined threshold (TH) (i.e., CL<TH), the CL in that portion of the baseline normal speech model can be classified as sufficiently low to justify a classification of "no confidence" in that portion of the baseline normal speech model, in which case, that portion of the baseline normal speech model would not be used until (and unless) its CL is improved through additional training data. If CL>TH, the CL in that portion of the baseline normal speech model can be classified as sufficiently high to justify using that portion of the baseline normal speech model to make comparisons to the person's actual speech to detect deviations in the actual speech from the baseline normal model. Many different predetermined TH levels can be provided. The various portions of the baseline normal speech model with CL>TH can be ranked from the highest CL>TH to the lowest CL>TH.

The above-described aspects of the invention further address the shortcomings of the prior art by saving and storing the person's actual speech recordings and those of one or more individuals similarly situated to the person, as well as the analysis of each of these recordings in a relatively permanent fashion, using blockchain technology. Blockchain is a digital and decentralized ledger that records information and transactions and can be used for collecting the speech recordings as well as the analysis of each of these recordings. By design, a blockchain is resistant to modification of the data. It is an open, distributed ledger that can record transactions between two parties efficiently and in a verifiable and permanent way. For use as a distributed ledger, a blockchain is typically managed by a peer-to-peer network collectively adhering to a protocol for inter-node communication and validating new blocks. Once recorded, the data in any given block cannot be altered retroactively without alteration of all subsequent blocks, which requires consensus of the network majority. Although blockchain records are not unalterable, blockchains may be considered secure by design and exemplify a distributed computing system with high Byzantine fault tolerance.

In more detail, a blockchain is a growing list of records, called blocks, which are linked using cryptography. Each block contains a cryptographic hash of the previous block, a timestamp and transaction data, etc. Blockchain technology offers a way for users to rely on a common digital history which is important because digital information and transactions are in theory easily faked and/or duplicated. Blockchain technology solves this problem without requiring a trusted intermediary. As such, by using this technology, users can confirm the recorded information and transactions without the need for a central certifying authority.

The use of blockchain technology facilitates continuous training and refinement of a person's "baseline" (i.e., the baseline normal speech model) by providing the machine learning and cognitive computing techniques with access to a relatively large sample of the person's speech recordings collected over time and the cognitive analysis thereof. Additionally, use of blockchain technology provides improved access to the stored speech recordings and analysis thereof for real-time retrieval and use by family members, caregivers, medical professionals and even the actual person, such as through mobile electronic communication devices like a smartphone, an electronic intelligent or virtual personal assistant such as the Amazon Alexa, etc.

Turning now to a more detailed description of aspects of the present invention, FIG. 1 depicts a system of speech detection and analysis according to an embodiment of the invention. FIG. 1 shows a person 100 from which speech is input to a device 300. For example, the device 300 can be a mobile communication device such as the person's smartphone or an intelligent or virtual personal assistant located in the person's non-clinical private environment like a home or regular living area. For example, the device 300 can be an instrument in a doctor's office where the speech (or an interview) is recorded and can be compared to the previous time the person visited the doctor. The device 300 includes an audio input 350 which receives the speech of the person 100.

In one or more embodiments, the device 300 can be triggered by the person's voice to collect speech of the person 100, while analysis of the collected speech occurs outside of the device 300 such as in a cloud computing environment. The device 300 can include a detector such as a sensor which detects the presence of the person's voice to start recording of the person's speech. For example, the device 300 can be an intelligent or virtual personal assistant located in the home or regular living area of the person 100, where the intelligent or virtual personal assistant is turned on to sample the voice or speech characteristics of the person's speech when the person's voice is sensed.

In one or more embodiments, the device 300 could be programmed to turn on at fixed intervals to sample the voice or speech characteristics within speech of the person 100, while analysis of the collected speech occurs outside of the device 300 such as in a cloud computing environment. For example, the device 300 can be a smartphone which is programmed to record the person's speech for a specified period of time using normal language or predefined sentences. By using an application on the smartphone, speech recording is turned on at specified times during a day or week to record the person's speech so that the person 100 would not have to separately enable the application.

In one or more embodiments, the device 300 can store the collected speech. In one or more embodiments, the collected speech can be stored and analyzed by one or more of a computing or processing device 200. The computing or processing device 200 is communicatively connected to the device 300. In accordance with aspects of the invention, the device 200 can be implemented as a NLP system having machine learning algorithms and classifier algorithms configured to perform operations in accordance with aspects of the invention.

A signal such as an audio or visual signal can be output from the device 300 in response to the information or results of the analysis from the computing or processing device 200. The signal can be provided to the person 100 from a signal output 460 of the device 300.

Collected speech, analysis thereof, and information and results of the analysis can be communicated to a user's device 400 from the computing or processing device 200. The computing or processing device 200 is communicatively connected to the user's device 400. For example, the user of the device 400 can be a family member, a caregiver or a medical professional participating in the care of the person 100. The user of the device 400 may not only view communicated information and results of the analysis of collected speech, but may also listen to an audio version of actual collected speech such as through an audio signal output 460 of the user's device 400. In one or more embodiments, the device 300 and the user's device 400 can be the same device. For example, as the user's device 400, a family member, a caregiver or a medical professional participating in the care of the person 100 can use the device 300 to access the baseline "normal" speech (i.e., the baseline normal speech model) of a person 100 even including the audio version thereof.

Collected speech, analysis thereof, and information and results of the analysis, such as a diagnosis of an illness, injury or disorder, can be stored or maintained on the computer or computer processing device 200. Based on the information and results of the analysis, in one or more embodiments, the computer or computer processing device 200 may take action by merely storing and maintaining the collected speech, the analysis thereof, and the information and results of the analysis. Based on the information and results of the analysis, in one or more embodiments, the computer or computer processing device 200 may take action by communicating or disseminating the collected speech, the analysis thereof, and the information and results of the analysis to one or more of the person 100, a family member, a caregiver or a medical professional participating in the care of the person 100. Based on the information and results of the analysis, in one or more embodiments, the computing or processing device 200 can initiate specific action related to the diagnosis of the illness, injury or disorder beyond merely storing and maintaining or disseminating the collected speech, the analysis thereof, and the information and results of the analysis.

In one or more embodiments, the computer or computer processing device 200 can be an external server, such as in a cloud computing environment, which can interface with a variety of different devices. In one or more embodiments, collected speech, analysis or comparison thereof, and information and results of the analysis and comparison, can be stored or managed in a relatively permanent fashion by using blockchain technology. The collected speech, analysis or comparison thereof, and information and results of the analysis and comparison, can be stored or managed in an electronically-accessible digital format and/or an electronically-accessible audio format by using the blockchain technology.

Figure 2:
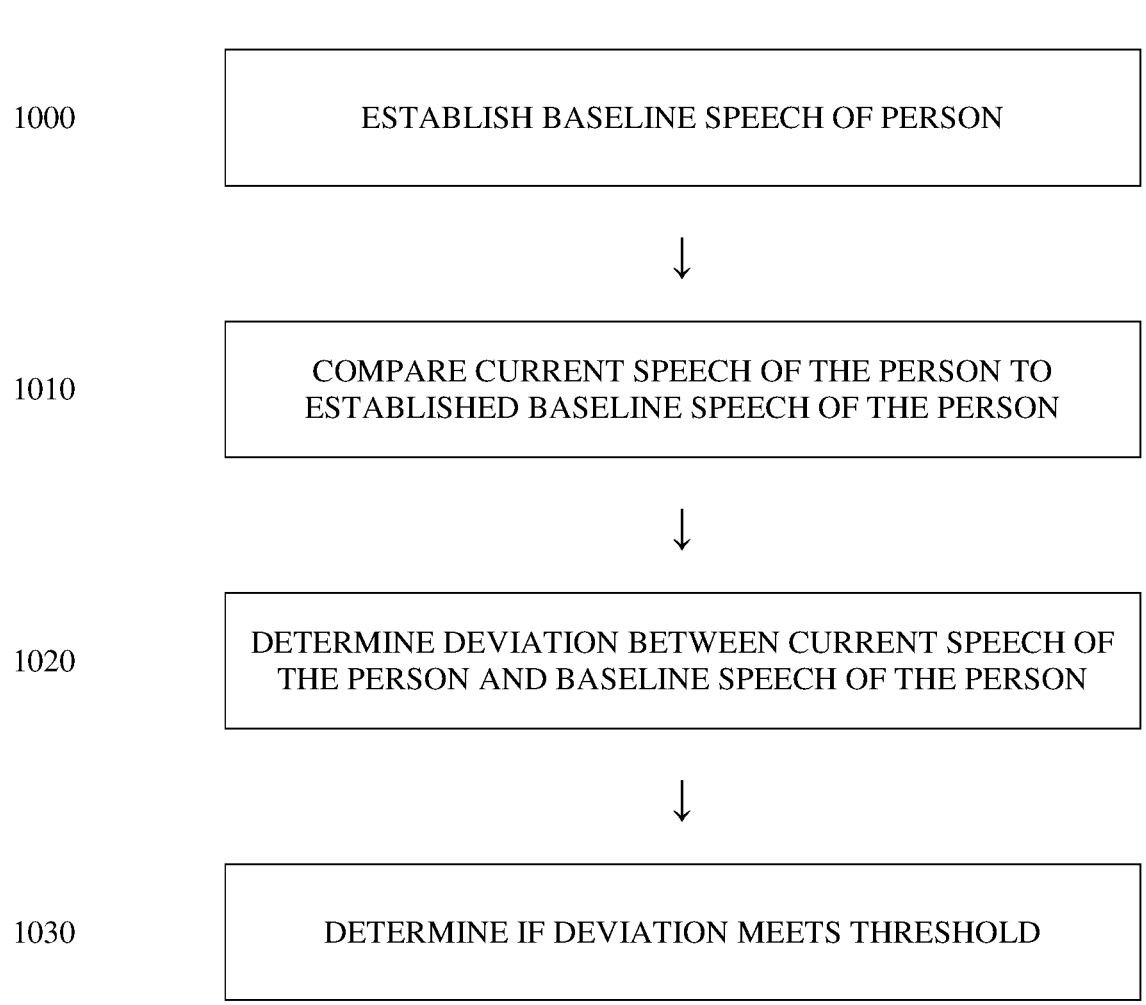
FIG. 2 depicts a flowchart of a method speech detection and analysis according to an embodiment of the invention.

FIG. 2 depicts a flowchart of a method of speech detection and analysis according to an embodiment of the invention. In one or more embodiments, the method of speech detection and analysis is a computer-implemented.

In 1000, for a person (100 in FIG. 1) whose speech is to be analyzed to diagnose a disorder, a baseline "normal" speech model is constructed or established. In one or more embodiments, the baseline "normal" speech model for a person is defined according to personal attributes of the person such as age, population, demographics, geographic location, dialect, existing illness, injury or disorder, existing speech impediment, natural progression of voice or speech (e.g., expected with aging due to tooth loss and compromised dentition, etc.) or a combination thereof.

The baseline "normal" speech model can define the absence or presence, the level, or rate of change of one or more property or characteristic in a person's speech.

In one or more embodiments, the baseline "normal" speech model can include the absence (e.g., zero level or zero degree) of a property or characteristic in a person's speech, outside of what is expected given the person's age, population, demographics, geographic location, dialect, existing illness, injury or disorder, existing speech impediment, natural progression of voice or speech or combination thereof. For example, after taking into account what speech is expected for a person, absence of aphasia, verbal apraxia, etc. which are common indications of stroke can be considered "normal" speech.

In one or more embodiments, the baseline "normal" speech model can include some presence (e.g., greater than zero level or greater than zero degree) of a property or characteristic in a person's speech, outside of what is expected, but still used as the baseline "normal" speech for a person. For example, for a first-ever recording of a person's speech, there may already be some presence of a property or characteristic in the person's speech. While this presence may indicate an illness when compared to a threshold for that illness, the presence of the property or characteristic in the person's speech also becomes the person's baseline "normal" speech from which to compare future speech recordings in determining illness progression.

In one or more embodiments, the baseline "normal" speech model can be constructed based on using machine learning algorithms to extract features from the person's recorded speech, which inherently reflects the person's age, population, demographics, geographic location, dialect, existing illness, injury or disorder, existing speech impediment or natural progression of voice or speech (e.g., expected with aging due to tooth loss and compromised dentition, etc.). For example, for a person who is diagnosed as having a stroke, the resulting verbal apraxia, etc. can become the baseline "normal" speech for that person from which any further changes in speech can be compared.

In one or more embodiments, the baseline "normal" speech model can be defined by one or more individual's recorded speech and analysis thereof, where the individual is similarly-situated to the person such as in age, population, demographics, geographic location, dialect, existing illness, injury or disorder, existing speech impediment or natural progression of voice or speech. Such individual baseline can hereinafter be referred to as a "cohort" baseline because the person and the similarly-situated individual are considered part of a group having one or more common characteristics (e.g., age, population, demographics, geographic location, dialect, existing illness, injury or disorder, existing speech impediment or natural progression of voice or speech, etc.).

The baseline "normal" speech model described above, can be constructed using automated machine learning and cognitive computing techniques that can extract and quantify relatively important metrics and properties present in recorded speech. As an example of such techniques, latent semantic analysis is a natural language processing technique that performs a high-dimensional associative analysis of semantic structure to detect common structures that occur in an individual's speech patterns. As another example, a data-driven component extraction algorithm such as independent component analysis can select relevant features that consistently predict deviation from a baseline, from among features within recorded speech.

Different analysis and extractions within the automated machine learning and cognitive computing techniques can be performed on a same recorded speech source. For example, spectrograms extracted from sound produced during a speech recording can be automatically analyzed using various information processing chains. For the same speech recording, syntactic and structural information can be automatically extracted from text produced by a speech-to-text conversion, then analyzed for features such as 'coherence', which are useful at discriminating neurological disease from healthy speech.

By using blockchain technology to store or manage in a relatively permanent fashion the collected speech, analysis thereof, and information and results of the analysis such as the "normal" baseline, a baseline of "normal" speech can be continuously refined because the machine learning and cognitive computing techniques provide an increased access to a relatively large sample of the person's speech recordings or the similarly-situated individual's speech recordings collected over time and the analysis of each of these speech recordings. That is, the baseline "normal" speech model is essentially continuously trained, updated and customized to the person whose speech is to be analyzed to diagnose a disorder such that even subtle changes or progression in the person's speech can be objectively detected and analyzed.

In 1010, the speech of the person is compared to the baseline "normal" speech model established for the person. More particularly, the real-time or current speech of the person is compared to the corresponding baseline "normal" speech model established for that person. In one or more embodiments, the absence or presence, the level and/or rate of change of one or more property or characteristic in the real-time or current speech of the person is compared to those in the "normal" speech baseline established for that person, to determine deviation from the "normal" baseline.

A deviation can represent a significant change beyond some threshold in the person's ability to speak, for example, verbal apraxia in stroke. Or, the deviation can be more subtle, for example, the forgetting of a pet's name, an important date, or the ability to recognize what an object is or what it is used for (agnosia) as is a symptom of Alzheimer's disease. For detection of symptoms typical of the mild stage of Alzheimer's disease, for example, deviations include the forgetting of familiar words, the location of everyday objects, general problems with memory and concentration, and trouble remembering new names. The deviations can occur slowly over time as is the case with different forms of dementia.

In one or more embodiments, the real-time or current speech can be a recording of the person's speech, such as the latest recording of the person's speech.

In one or more embodiments, the real-time or current speech can be the active or actual speech of a person observed by someone like a family member, a caregiver or a medical professional participating in the care of the person. For example, a doctor who is located in the person's immediate physical environment can be observing active speech of the person during the person's visit to the emergency room or to the doctor's office.

In one or more embodiments, the computer or computer processing device (200 in FIG. 1) performs the comparison of the real-time or current speech of the person to the corresponding baseline "normal" speech established for that person. In one or more embodiments, the computer or computer processing device can employ the machine learning and cognitive computing techniques described above to compare the real-time or current speech of the person to the corresponding baseline "normal" speech established for that person.

In one or more embodiments, someone like the family member, the caregiver or the medical professional participating in the care of the person can compare the real-time or current speech of the person to the corresponding baseline "normal" speech established for that person. For example, whether located in the person's immediate physical environment or located remotely from the person's immediate physical environment, a doctor which employs the user's device (400 in FIG. 1) described above can listen to an audio version of the actual speech recording of the baseline "normal" speech for the person via the user's device, where such speech recording is from the person's recorded speech or from a similarly-situated individual's recorded speech. In one or more embodiments, the doctor can listen to an audio version of one or both of the baseline "normal" speech recordings among the person's recorded speech and the similarly-situated individual's recorded speech.

As similarly discussed above, by using blockchain technology to store or manage in a relatively permanent fashion the actual speech recording of the baseline "normal" speech for the person, access to the baseline "normal" speech for the family member, the caregiver or the medical professional comparing the real-time or current speech of the person to the corresponding baseline "normal" speech established for that person can be increased. By increasing access to the actual speech recording of the baseline "normal" speech for the person, the family member, the caregiver or the medical professional can have an objective example of a person's "normal" speech from which even subtle changes or progression in the person's real-time or current speech can be observed. Furthermore, using blockchain would allow the recorded speech and deviations to be stored in a relatively permanent fashion which could be useful for a family member or a caregiver or for a medical professional in the case of a lawsuit.

In 1020, as information or results of the above-described comparison, a deviation between the real-time or current speech of the person and the baseline "normal" speech model established for the person is determined. In one or more embodiments, the computer or computer processing device which performs the comparison of the real-time or current speech of the person to the corresponding baseline "normal" speech established for that person determines the deviation. The computer or computer processing device can employ the machine learning and cognitive computing techniques described above to determine the deviation between the real-time or current speech of the person and the corresponding baseline "normal" speech established for that person.

In one or more embodiments, the family member, the caregiver or the medical professional who performs the comparison of the real-time or current speech of the person to the corresponding baseline "normal" speech established for that person determines the deviation.

In one or more embodiments, the deviation can be expressed by a difference in the absence or presence, the level, or rate of change of one or more property or characteristic between the real-time or current speech of the person and the corresponding baseline "normal" speech established for that person.

In one or more embodiments, the deviation from the comparison of the real-time or current speech of the person to the corresponding baseline "normal" speech established for that person, can be stored or maintained on the computer or computer processing device. In one or more embodiments, speech could be recorded in the block (e.g., within Blockchain technology) when the deviation exceeds a threshold and the rate of recording in the block could be connected to the rate at which the speech deviates from the threshold.

As similarly discussed above, by using blockchain technology to store or manage in a relatively permanent fashion the collected speech, analysis and comparison thereof, and information and results of the analysis and comparison such as deviation from "normal" baseline, a baseline "normal" speech can be continuously refined because the machine learning and cognitive computing techniques are provided with increased access to a relatively large sample of the person's speech recordings or the similarly-situated individual's speech recordings collected over time and the analysis of each of these speech recordings. Again, the baseline "normal" speech is essentially continuously updated and customized to the person whose speech is to be analyzed by a medical professional. Furthermore, using blockchain technology would allow the recorded speech and deviations to be stored in a relatively permanent fashion which could be useful for a family member or a caregiver or for a medical professional in the case of a lawsuit.

In 1030, the deviation is compared to an established threshold to determine if the deviation meets or exceeds the established threshold. In one or more embodiments, the computer or computer processing device which determines the deviation compares the deviation to the established threshold. In one or more embodiments, the family member, the caregiver or the medical professional which determines the deviation compares the deviation to the established threshold.

A different threshold could be established for different medical conditions, for different personal attributes, for different "cohort" groups in which individuals have one or more common characteristic, etc. The threshold can be expressed in terms of the absence or presence, the level, the rate of change of one or more property or characteristic in a person's speech, differences in any one of the absence or presence, the level, the rate of change of one or more property or characteristic, or a deviation from an established threshold of the absence or presence, the level, the rate of change of one or more property or characteristic. For example, a change to presence of aphasia, verbal apraxia, etc. from absence thereof can define a threshold for abnormal speech relative to a stroke. For example, a change of the absence or presence, the level, the rate of change of one or more property or characteristic in a person's speech, which is expected due to an existing speech impediment or natural progression of voice or speech (e.g., due to aging, tooth loss, compromised dentition, etc.) may not define a threshold for abnormal speech relative to an illness, injury or disorder such as stroke. For example, the deviation from an established threshold of a property or characteristic in speech of a "cohort" individual similarly-situated to a person may define a threshold for abnormal speech relative to dementia or may merely define a threshold for normal aging.

In one or more embodiments, the deviation defined for a same real-time or current speech of a person can be compared to one or more established threshold at substantially a same time. A deviation of a property or characteristic in a person's speech which is beyond a threshold for one illness, injury or disorder may not be beyond a threshold for another illness, injury or disorder.

As similarly discussed above, by using blockchain technology which is resistant to modification to store or manage in a verifiable and relatively permanent fashion the deviation from "normal" baseline, efficient comparison of the deviation to multiple thresholds can be performed such that subtle changes or progression in the person's speech for a number of illnesses, injuries or disorders can be objectively detected.

In one or more embodiments, if the threshold is met or exceeded, the computer or computer processing device initiates action directly related to the illness, injury or disorder.

In one or more embodiment where the threshold is met or exceeded, the computing or processing device (200 in FIG. 1) can initiate notification of a doctor, emergency services or a family member or could call a help line, etc. depending on the severity and rate of change of a property or characteristic in a person's speech.

In one or more embodiment where the threshold is met or exceeded, the computing or processing device (200 in FIG. 1) can adjust frequency of turn on-turn off times of the device (100 in FIG. 1), to increase/changing time of day for collection, especially where deviations from the "normal" baseline exceed a threshold. For example, the rate of recording by the device could be adjusted to correspond to the rate at which the speech deviates from the threshold.

In one or more embodiment where the threshold is met or exceeded, the computing or processing device (200 in FIG. 1) can prompt proactive treatment related to such diagnosis. For example, the computing or processing device can provide prompts to the person via the device (100 or 400 in FIG. 1) to elicit speech from the person. The prompts can include interactive exercises that specifically use tests for memory and concentration or are designed for treatment related to an illness, injury or disorder such as speech impediments due to a stutter. For example, the prompts can include recorded speech which is played back in an audio version to facilitate treatment of the stutter. Providing the prompt for proactive treatment related would further allow refinement of the baseline "normal" speech of the person by highlighting deviations which exist due to stutters, for example, and are not abnormal deviations that should trigger a notification for diagnosis of a more serious illness, injury or disorder.

In one or more embodiment where the deviation does not meet or exceed the threshold, the computer or computer processing device 200 may not initiate action directly related to the illness, injury or disorder. For example, the last-recorded speech of the person can be merely saved as a new baseline "normal" speech established for the person from which to compare a later-recorded speech of the person.

Figure 3:
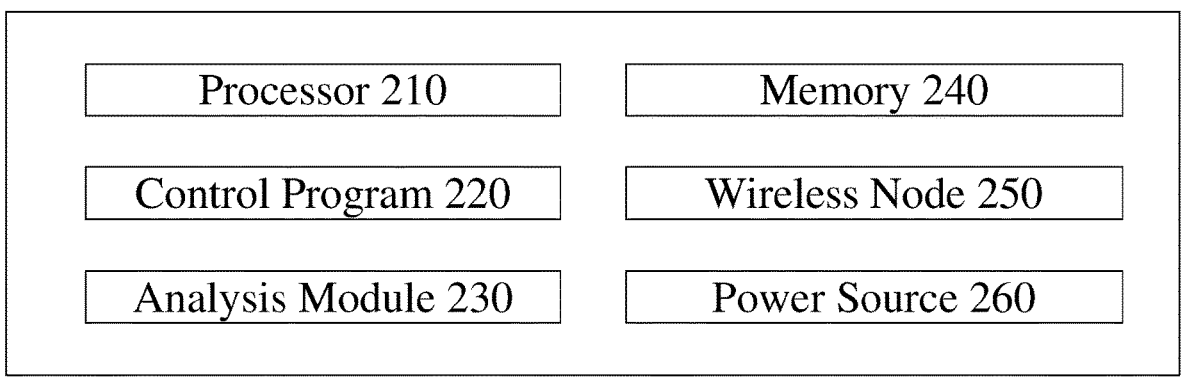
FIG. 3 depicts major hardware of a processing device according to an embodiment of the invention.

FIG. 3 depicts the major hardware components of the computer or computer processing device (200 in FIG. 1) according to an embodiment of the present invention. In one or more embodiments, the computer or computer processing device stores and/or manages collected recorded speech, analysis and comparison thereof, and information and results of the analysis and comparison by using blockchain technology.

A programmable processor 210 executes a computer control program 220 to store and/or manage the collected recorded speech, analysis and comparison thereof, and information and results of the analysis and comparison.

The analysis module 230 performs analysis of the collected recorded speech, such as by machine learning and cognitive computing techniques. The analysis module 230 can construct and refine a "normal" baseline corresponding to a person (1000 in FIG. 2), compare real-time or current speech of the person to the corresponding baseline "normal" speech (1010 in FIG. 2), determine a deviation from the comparison between the real-time or current speech of the person and the corresponding baseline "normal" speech (1020 in FIG. 2) and determine if the deviation meets a threshold (1030 in FIG. 2).

The memory 240 stores the recorded collected speech, analysis and comparison thereof, and information and results of the analysis and comparison which are variously generated in 1000 through 1030 of FIG. 2. Collected recorded speech, prompts such as interactive exercises, etc. are variously communicated between the computer or computer processing device and other devices connected thereto, via a wireless node 250, which can include any sort of remote connection. The wireless node 250 allows the computer or computer processing device to be connected to other devices such as the device (300 in FIG. 1) and the user's device (400 in FIG. 1). In other embodiments of the present invention, traditional wire systems can be used. The computer or computer processing device can include a power source 260 which can be a battery, electric feed, or any other method known in the relevant art.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A natural language processing system for analyzing speech, the system comprising:
    a computer processing device configured to receive recorded speech of a person, wherein the computer processing device:
        constructs a baseline speech model of the person, the baseline speech model of the person comprising a property of speech based on a personal attribute of the person, the baseline speech model comprising the recorded speech for the person;
        ranking portions of the baseline speech model itself using confidence intervals prior to a comparison for a deviation of the property of speech, the ranking of the portions preventing low-ranked portions of the recorded speech for the person from being used for subsequent comparisons for determinization of a disorder;
        compares current recorded speech of the person to the baseline speech model of the person to determine the deviation of the property of speech there between; and
        determines if the deviation of the property of speech meets a threshold of the property of speech that is defined for the disorder; wherein:
    the computer processing device constructs the baseline speech model of the person by using machine learning and cognitive computing techniques with which the property of speech is extracted and quantified from a speech recording;
    the speech recording comprises recorded speech of an individual person having a common personal attribute with the person; and
    the property of speech based on the personal attribute of the person within the baseline speech model of the person is defined from the analyzed recorded speech of the individual person having the common personal attribute with the person, the speech recording comprising a plurality of recorded speeches of the person that are taken over a period of time.

2. The system of claim 1, wherein the computer processing device further stores the recorded speech of the person and the baseline speech model of the person using blockchain technology.

3. The system of claim 2, wherein the computer processing device further stores an electronically accessible audio version of the baseline speech model of the person by using the blockchain technology.

4. The system of claim 1, wherein the personal attribute of the person comprises age, population, demographics, dialect, an existing illness, injury, disorder, speech impediment, and natural progression of voice that is due to any of the aforementioned personal attributes.

5. The system of claim 1, wherein: the property of speech based on the personal attribute of the person within the baseline speech model of the person is defined from the analyzed plurality of recorded speeches of the person.

6. The system of claim 1, wherein the computer processing device that determines that the deviation of the property of speech meets the threshold of the property of speech that is defined for the disorder, further determines a communication directly related to the disorder, and
the communication directly related to the disorder comprises an interactive exercise that elicits additional recorded speech from the person to provide speech therapy to the person.

7. The system of claim 6, wherein the disorder for which the speech therapy is provided to the person comprises one or more of:
a speech impediment comprising stuttering, and
a neurological disorder or brain-related disorder comprising one or more of stroke, Alzheimer's disease, Parkinson's disease and dementia.

8. The system of claim 1, wherein the computer processing device that determines that the deviation of the property of speech meets the threshold of the property of speech that is defined for the disorder, further determines a communication directly related to the disorder, and
the communication directly related to the disorder comprises the diagnosis of a neurological disorder, brain-related illness or brain-related injury of the person.

9. The system of claim 1, wherein the property of speech further comprises cadence, tone, speed, periodicity, and volume word content, word complexity, semantic structure, sound produced during speech and coherency.

10. A computer-implemented method that processes natural language for analyzing speech, the computer-implemented method comprising:
receiving recorded speech of a person;
constructing a baseline speech model of the person, the baseline speech model of the person comprising a property of speech based on a personal attribute of the person, the baseline speech model comprising the recorded speech for the person;
ranking portions of the baseline speech model itself using confidence intervals prior to a comparison for a deviation of the property of speech, the ranking of the portions preventing low-ranked portions of the recorded speech for the person from being used for subsequent comparisons for determinization of a disorder;
comparing current recorded speech of the person to the baseline speech model of the person to determine the deviation of the property of speech therebetween; and
determining if the deviation of the property of speech meets a threshold of the property of speech that is defined for the disorder; wherein:
a computer processing device constructs the baseline speech model of the person by using machine learning and cognitive computing techniques with which the property of speech is extracted and quantified from a speech recording;
the speech recording comprises recorded speech of an individual person having a common personal attribute with the person; and
the property of speech based on the personal attribute of the person within the baseline speech model of the person is defined from the analyzed recorded speech of the individual person having the common personal attribute with the person, the speech recording comprising a plurality of recorded speeches of the person that are taken over a period of time.

11. The computer-implemented method of claim 10 further comprising storing the recorded speech of the person and the baseline speech model of the person using blockchain technology.

12. The computer-implemented method of claim 10, wherein the property of speech based on the personal attribute of the person within the baseline speech model of the person is defined from the analyzed plurality of recorded speeches of the person.

13. The computer-implemented method of claim 10, wherein determining that the deviation of the property of speech meets the threshold of the property of speech that is defined for the disorder comprises determining a communication directly related to the disorder, and
the communication directly related to the disorder comprises an interactive exercise that elicits additional recorded speech from the person to provide speech therapy to the person.

14. A computer program product which processes natural language for analyzing speech, the computer program product comprising a computer readable storage medium having program instructions embodied therewith, wherein the program instructions are executable by a computer to cause the computer to perform a method comprising:
receiving recorded speech of a person;
constructing a baseline speech model of the person, the baseline speech model of the person comprising a property of speech based on a personal attribute of the person, the baseline speech model comprising the recorded speech for the person;
ranking portions of the baseline speech model itself using confidence intervals prior to the any comparison for diagnosis, the ranking of the portions preventing low-ranked portions of the recorded speech for the person from being used for subsequent comparisons for diagnosis;
comparing current recorded speech of the person to the baseline speech model of the person to determine the deviation of the property of speech therebetween; and
determining if the deviation of the property of speech meets a threshold of the property of speech that is defined for the disorder; wherein:
the computer constructs the baseline speech model of the person by using machine learning and cognitive computing techniques with which the property of speech is extracted and quantified from a speech recording;
the speech recording comprises recorded speech of an individual person having a common personal attribute with the person; and
the property of speech based on the personal attribute of the person within the baseline speech model of the person is defined from the analyzed recorded speech of the individual person having the common personal attribute with the person, the speech recording comprising a plurality of recorded speeches of the person that are taken over a period of time.

15. The system of claim 1, wherein ranking the portions of the baseline speech model using the confidence intervals is performed by a classifier.

16. The system of claim 1, wherein:
the baseline speech model is of the recorded speech of the person in advance of the current recorded speech used to determine the deviation of the property of speech; and
based on a threshold not being met for a confidence interval of a portion of the baseline speech model, a classifier is configured to classify the portion of the baseline speech model as being unusable until the confidence interval of the portion improves.

* * * * *